United States Patent [19]

Kalinski et al.

[11] Patent Number: 5,179,818
[45] Date of Patent: Jan. 19, 1993

[54] OVAL WRAP SUTURE PACKAGE

[75] Inventors: Robert J. Kalinski, Milford, N.J.; Robert J. Cerwin, Pipersville, Pa.; Marvin Alpern, Glen Ridge, N.J.

[73] Assignee: Ethicon, Inc., Somerville, N.J.

[21] Appl. No.: 832,278

[22] Filed: Feb. 7, 1992

Related U.S. Application Data

[62] Division of Ser. No. 541,222, Jun. 20, 1990, Pat. No. 5,099,999, which is a division of Ser. No. 236,057, Aug. 24, 1988, Pat. No. 4,961,498.

[51] Int. Cl.⁵ .................. B65B 63/04; A61B 17/06
[52] U.S. Cl. .................................. 53/430; 53/409
[58] Field of Search ............ 53/430, 116, 204, 409; 206/63.3

[56] References Cited

U.S. PATENT DOCUMENTS

| 3,167,895 | 2/1965 | Egler et al. ............... 53/430 X |
| 3,490,192 | 1/1970 | Regan, Jr. ...................... 53/430 |
| 3,959,947 | 6/1976 | Sonnino ...................... 53/430 X |
| 4,424,898 | 1/1984 | Thyen et al. ............... 206/63.3 |
| 4,967,902 | 11/1990 | Sobel et al. ............... 206/63.3 |

Primary Examiner—James F. Coan
Attorney, Agent, or Firm—Paul A. Coletti

[57] ABSTRACT

A molded two-piece suture package is disclosed which encloses and defines an oval channel in which sutures may be wound. The oval channel has two semicircular end sections connected by straight side sections. An opening in the channel is provided at the juncture of a straight section and an end section, permitting sutures to be withdrawn from the channel at the end of a straight section. In a preferred embodiment the interior wall of the channel is formed by alternating engaging sections formed in the respective package pieces. To prevent the wrapped suture from becoming entrapped when the two pieces are engaged, the top and bottom of the channel is alternately raised and lowered in alignment with the alternating wall sections, causing the wound suture to bridge those areas where it may become entrapped between the mating package pieces. Entrapment of the suture end at the outside of the channel is prevented by alternately recessing the outer wall of the channel. Flexible molded needle parks are also disclosed for the package.

4 Claims, 9 Drawing Sheets

OVAL WRAP SUTURE PACKAGE

This is a division of application Ser. No. 541,222, filed Jun. 20, 1990, now U.S. Pat. No. 5,099,994, which is a division of Ser. No. 236,057, filed Aug. 24, 1988, now U.S. Pat. No. 4,961,498, which is hereby incorporated by reference.

This invention relates to holders for needles and, in particular, to holders and packages which provide for the delivery of sutures containing attached needles.

In the packaging of surgical needles including surgical needles to which there are attached sutures, it is important that the needle and its attached suture be easily removable from the package in one smooth motion. When the needle is grasped by a forceps and pulled, the needle should easily release from the Package and the suture should withdraw from the package smoothly without binding or snagging in the package, and without becoming entangled. Also, suture materials, particularly monofilaments such as catgut, polydioxanone and the like, especially the heavier deniers, are known to take a set during storage; i.e., they tend to have a "memory" causing them to retain the shape of their position in the package after removal from the package. Hence the package should be designed so that any tight bends or curves required in order to package the suture be eliminated.

It is further desirable for suture packages to be economical to manufacture in volume quantities. A manufacturing process directed toward this end is one in which the suture package is formed of two interlocking molded, stamped, or thermoformed polymeric members. Packages made in such a process enable the formation of projections useful for winding and capturing the suture in channels designed for that purpose. These packages also enable the maintenance of fine tolerances necessary in the formation of a precision design.

Packages for armed sutures; i.e., sutures where the needle is attached, are disclosed, for example, in U.S. Pat. Nos. 4,135,623; 4,034,850; and 3,857,484. A molded package for armed sutures is disclosed in U.S. Pat. No. 4,424,898. Also, packages for use with the heavier denier monofilament sutures which provide a package which substantially reduces undesirable suture "memory" of the suture are described in U.S. Pat. No. 3,972,484.

In accordance with the principles of the present invention, a needle and suture holder is described which forms an oval-shaped channel for retention of the suture. One end of the suture exits the oval channel toward the center of the oval and is attached to a needle located in the center of the oval. The oval channel includes gently rounded end sections, eliminating any tight bends or curves which would induce undesirable suture "memory". In a preferred embodiment, the suture exits the oval at the juncture of a lesser arcuate side section of the channel and a rounded end section. This allows the suture to be withdrawn from the lesser arcuate side section rather than from the rounded end section, thereby minimizing resistance to withdrawal of the suture from the package.

It has been found that when a channeled suture package is formed of two interlocking pieces, mislocation of the suture toward an edge of the channel where the mating pieces come together will cause the suture to become pinched or entrapped between the mating pieces. In accordance with the principles of a preferred embodiment of the present invention, a surface of the channel contains periodic projections toward the center of the channel. The suture will then "bridge" the surface of the channel intermediate these projections as it traverses the channel and hence can bridge the entrapping areas of the channel. The projections and corresponding wall areas also eliminate any continuous interlocking edges in the channel where the suture material can become entrapped as the two pieces of the package are interlocked together.

Figure 1:
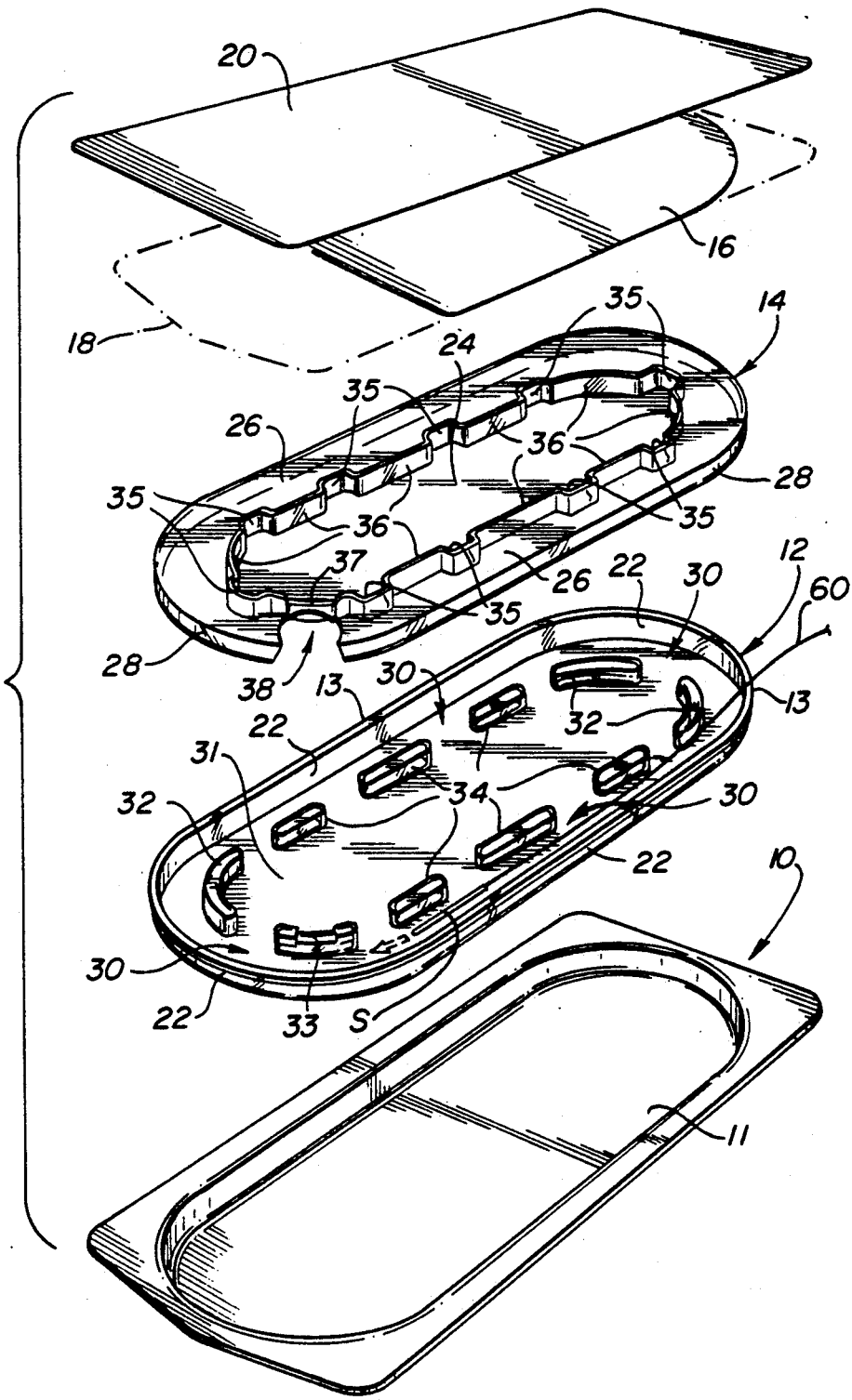
FIG. 1 illustrates the assembly of a suture package constructed in accordance with the principles of the present invention.

Referring first to FIG. 1, an assembly drawing of an oval suture package of the present invention is shown. The package is sealed in a foil overwrap which includes a mechanically formed bottom foil tray 10. A dish-like area 11 is formed in the center of the tray to hold the suture package. Sutures made of synthetic material such as Vicryl or polydioxanone have been found to degrade in the presence of excessive moisture over time. A sealed foil overwrap has been found to prevent moisture penetration of the package. Sutures made of natural materials such as catgut do not degrade in the presence of moisture and hence may be enclosed in moisture permeable overwraps, and may even be packaged in solution.

Located within the dish-like area 11 of the foil tray 10 is a two-piece molded suture package including a top piece 14 and a bottom piece 12. Formed in the package bottom 12 are a number of molded straight and curved lugs 34, 33, and 32 which define the inner wall of a suture wrapping channel 30. The suture wrapping channel is also defined by the floor 31 of the bottom piece 12. The bottom piece 12 has an outer wall 22. At the top edge of the outer wall 22 is a sealing flange 13 which may be sealed to the overlying overwrap material.

The top piece 14 of the suture package fits inside the bottom piece. The outer wall 28 of the package top fits inside the outer wall 22 of the package bottom and defines the outer wall of the suture wrapping channel 30. The package top 14 has an upper surface 26 inside of which is formed a depressed central area 24. The depressed central area 24 rests on the floor 31 of the package bottom when the two pieces are mated together. The outer wall of the central area 24 is molded in an irregular shape to fit around the lugs of the bottom piece. Wall sections 36 are recessed to fit inside of the lugs, and sections 35 project to extend between the lugs to form portions of the inner wall of the suture wrapping channel 30. At one end of the package the outer wall 28 and the upper surface 26 are cut away as shown at 38 to permit the suture to exit the suture wrap channel to the interior of the package. A small section 37 of the upper surface 26 is depressed to fit inside the depression of the lug 33, enabling the suture to pass to the interior of the package through the depression of the section 37.

FIG. 1 shows several types of overwraps which may be used with the suture package. One is a foil label 16 which overlies a major portion of the package when the package is to be enclosed in a single overwrap. The label 16 will leave the corner of the package where the suture exits the wrapping channel at 37 exposed. Optionally the package may be enclosed on the top by a peelable inner foil lid 18, which is sealed to the flange of the foil tray 10. When a double overwrap is used, an inner foil lid 20 is sealed to the flange of the foil tray 10 and the foil sealed package is then sealed inside a paper or paper and plastic overwrap (not shown). As yet another option, a peelable, breathable paper lid may be sealed to the tray flange and the sealed package enclosed in a clear plastic overwrap.

Figure 2:
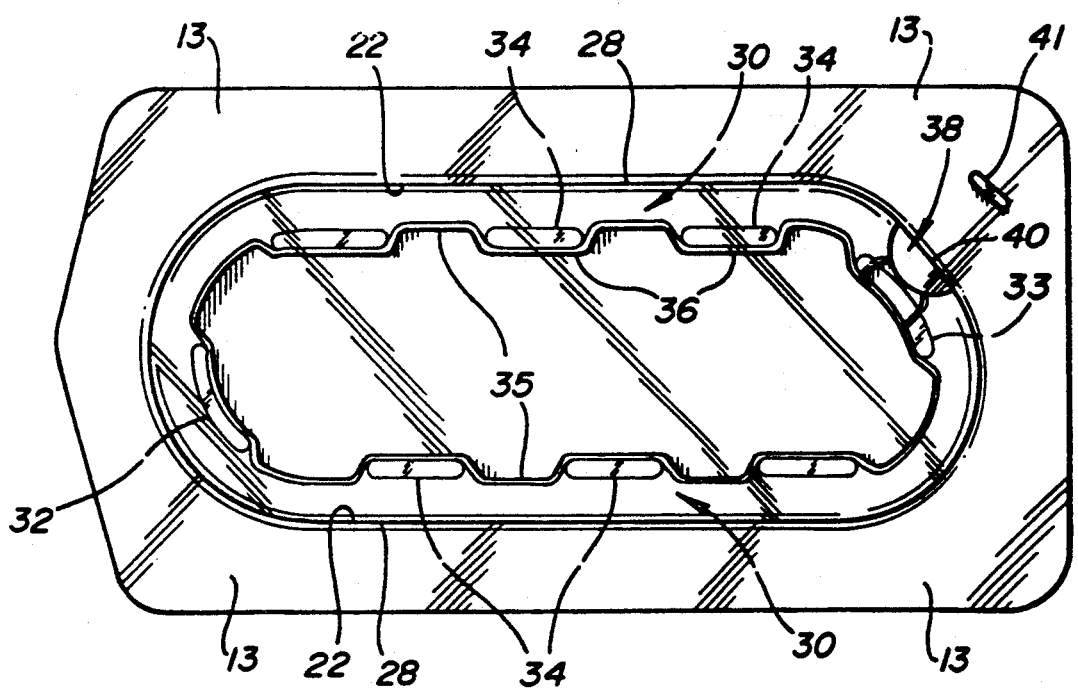
FIG. 2 is a plan view of an oval suture package with a peel tab corner.

An alternate embodiment of the top and bottom package pieces 10 and 12 is shown in FIG. 2. In this embodiment one end of the oval channel is slightly flattened at 40 where the suture exits the channel 30 at the cutaway 38. The flattening of the oval at 40 leaves space at the corner of the package bottom flange 13 for a peel tab projection 41 which is molded in the flange. When the inner foil lid is sealed to the flange 13, it is sealed about the periphery of the channel 30, and in particular between the projection 41 and the flattened portion of the oval channel. An unsealed corner of the foil lid will then rest on the projection 41, raised above the surface of the flange 13 by this projection. The corner of the lid is thus visibly separated from the flange, enabling the user to easily identify the corner of the lid which is to be grasped when the lid is to be peeled off of the package.

FIG. 2 clearly shows the suture wrapping channel 30 defined by the outer wall 28 of the package top. The inner wall of the channel 30 is defined by the outer sides of the straight lugs 34 and the curved lugs 32 at the ends of the oval, which are molded to project from the bottom piece 12. The inner wall of the channel 30 is also defined by the projections 35 of the top piece 14, which extend between the lugs 32, 33, and 34.

Figure 3:
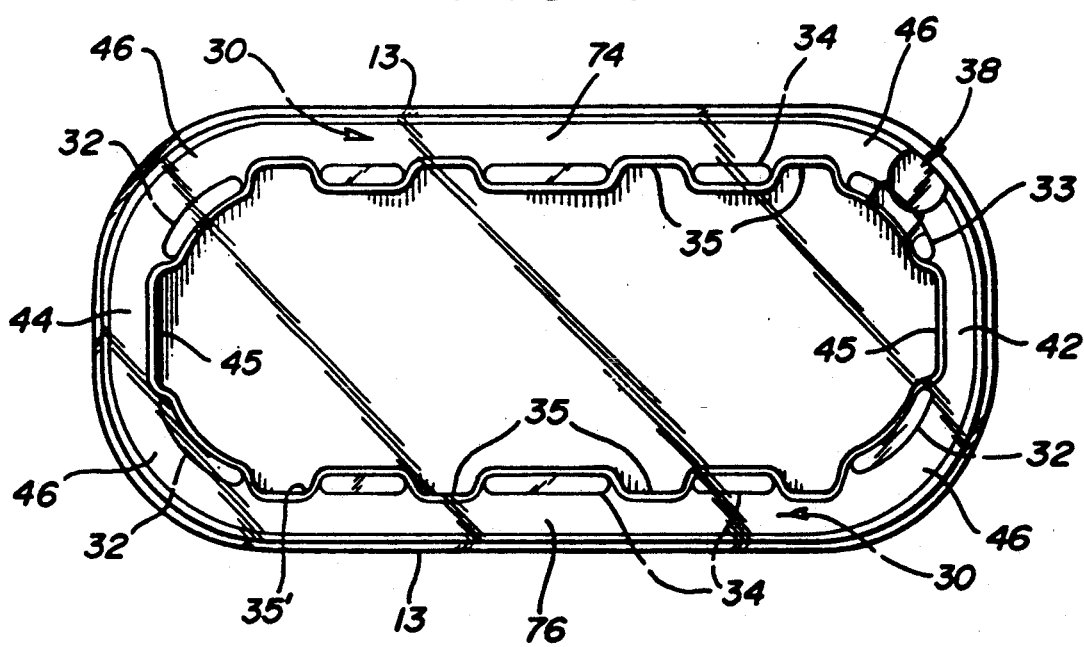
FIG. 3 is a plan view of an oval suture package of the present invention with two long straight sides and two short straight sides.

In the embodiment of FIG. 3 the suture wrapping channel has been enlarged to accommodate a longer suture. In the previous embodiments the oval channel comprised two long, straight sides connected by semicircular ends. In the embodiment of FIG. 3 the suture wrapping channel comprises two long sides 74 and 76 at the top and bottom of the FIGURE and two shorter straight sides 42 and 44 at the ends of the oval. The two shorter straight sides 42 and 44 are connected to the longer straight sides 74 and 76 by quarter-circular channel corners 46. It may be seen that in this embodiment the projections 45 extending from the top piece 14 between the curved lugs 32 define straight interior walls for the channel 30.

Figure 4:
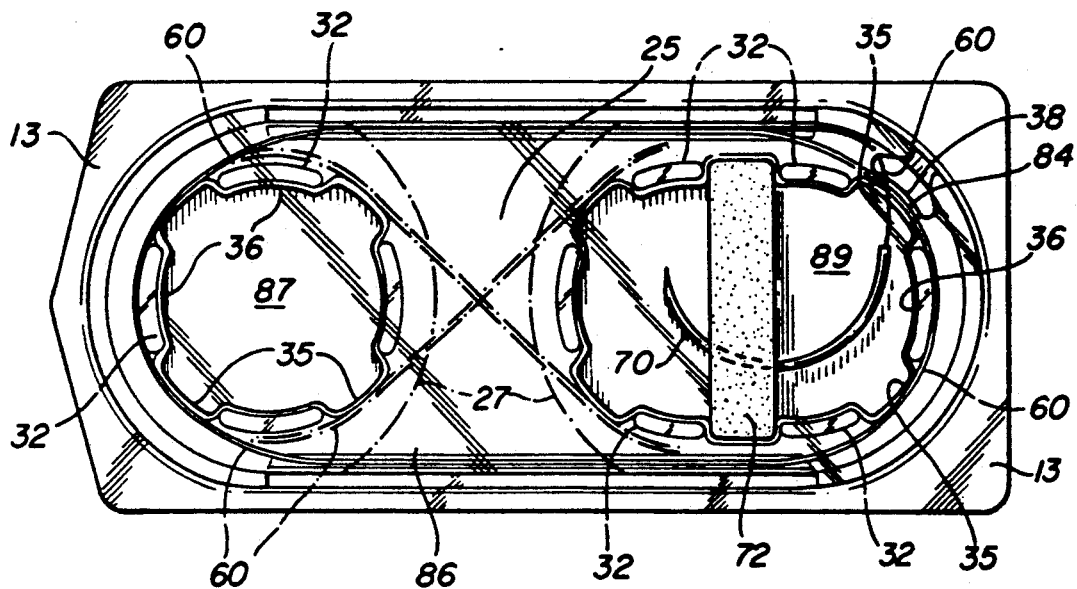
FIG. 4 is a plan view of an oval suture package with a central depressed area at each end of the oval.

In the embodiment of FIG. 4 the narrowest dimension of the oval suture wrapping channel is only defined at the ends of the oval by a circular and an oval lug pattern. A suture filament 60 is seen wound around these lug patterns in the channel and exits the channel at the cutout 38 in the top piece 14. The exiting end of the suture filament 60 is swaged to the bore of a curved needle 70. The needle 70 is retained in the depressed area 89 in the inside of the lugs at the suture-exiting end of the package in a needle park 72, formed by a piece of foam which is adhesively attached inside the depressed area 89. The top piece 14 of the package is attached to the bottom piece 12 where the depressed areas 87 and 89 of the top piece 14 contact the central area 31 of the bottom piece 12. The method of attachment may be by means of an adhesive, heat sealing or mechanical attachment. Between the depressed areas 87 and 89 the upper surface 86 of the package formed by the top piece is substantially coplanar with the flange 13 of the bottom piece 12. Thus, the narrowest dimension of the wrapping channel 30 is defined only at the oval ends of the package. At one end of the oval channel is a lug 82 with a molded depression, similar to the depression molded in the curved lug 33 of FIG. 1. A depression 84, similar to depressed section 37 in FIG. 1, is formed in the top piece 14 just to the inside of the cutout 38, to enable the suture filament to exit the channel and enter the depressed central area 89 at a level below the top surface of the package.

The embodiment of FIG. 4, unlike the previous embodiments, does not have a continuous depressed central floor area 24 in the top piece 14 which contacts the surface of the depressed central floor 31 of the bottom piece 12. Instead, only the two areas 87 and 89, encircled by lugs 32, are depressed. The remainder of the top piece inside the channel and surrounding the areas 87 and 89 is raised to the level of the flange 13 of the bottom piece. Thus, there is a cavity between the top piece surface 25 and the central floor area 31 of the bottom piece which surrounds the depressed areas 87 and 89. This cavity may be used to enclose a suture filament which is wound around the two depressed areas in a figure-8 pattern instead of the oval winding pattern. The cross-over point of the figure-8 pattern will be within the cavity space between the two depressed areas. The suture filament may be wound around the lugs 32 prior to assembly of the two package pieces or, alternatively, the suture filament may be wound through the package after assembly by a filament-carrying stylus which is inserted into the channel 30 between the two pieces at the outer peripheral wall of the channel. If the stylus technique is used, it is necessary to form an opening across the center of the top piece surface 25 to enable traversal of the stylus across the interior of the package. Dashed lines 27 mark cut lines for removal of a section of the top surface 25, thereby enabling the stylus to traverse the central area of the package when winding a suture filament through the assembled package in a figure-8 pattern.

Figure 5:
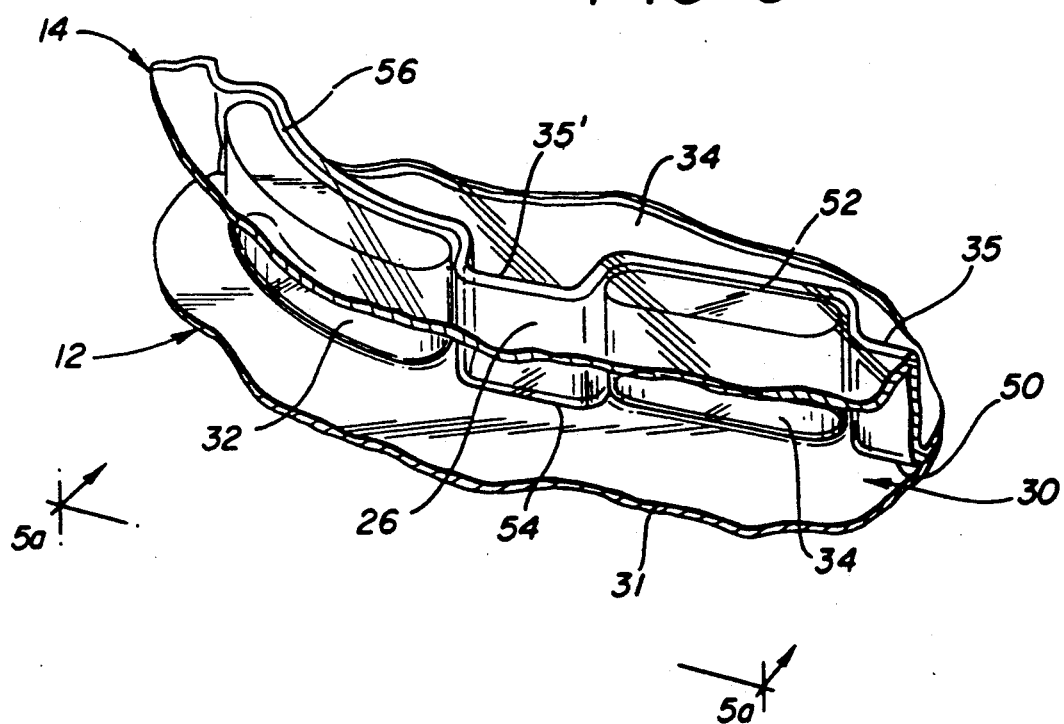
FIG. 5 is an enlarged view of the suture wrapping area of a suture package illustrating suture catching mating edges.

FIG. 5 is an enlarged view of the suture wrapping channel 30 of a suture package, and specifically an enlargement of the inner channel wall projection 35' of FIG. 3 and lugs 32 and 34 on either side of projection 35'. FIG. 5 shows the planar floor 31 of the channel 30 and lugs 32 and 34, all of which are formed in the bottom piece 12 of the suture package. The inner wall of the channel is also formed by the mating projections 35' and 35 of the top piece 14 of the suture package. The top of the channel 30 is defined by the upper surface 26 of the top piece 14, which extends from the top of the projections 35' and 35 and over the lugs 32 and 34.

It has been found that a problem can arise when mating the top and bottom pieces of the suture package in this manner. Before the two pieces are mated together, the suture filament is wound around the lugs in the package bottom 12 in its oval pattern. As an alternative and currently preferred method of winding the suture filament in the channel, the two package pieces are first mated together and the suture filament is wound through the channel by a stylus inserted into the bottom of the channel between the outer walls 22 and 28 of the mated package pieces. The winding of the suture in either case can result in location of the suture filament in contact with the lugs at the inside of the channel, particularly at the oval ends of the package. In the instance of the first technique, when the top piece is placed inside and over the bottom piece, the mating edges of the lugs with the top of the channel and the mating edges of the projections with the floor of the channel can catch and pinch the suture filament in these locations. The mating edges of the lugs and top of the channel are indicated at 52 and 56, and the mating edges of the projections and the floor of the channel are indicated at 50 and 54. The two package pieces are then adhesively attached in the center of the oval, leaving the suture filament pinched between these mating edges. When the suture filament is later pulled from the package for surgical use, the filament will pull and snag where it is pinched in these mating edges. In the case of both the stylus winding technique and the pre-closure winding technique, when the suture is pulled from the package a "capstan" phenomenon will occur as the suture filament tightens around the inner wall of the channel as it is pulled. The tightening of the suture filament against the inner wall of the channel will cause the filament to enter and bind between the mating edges.

Figure 6:
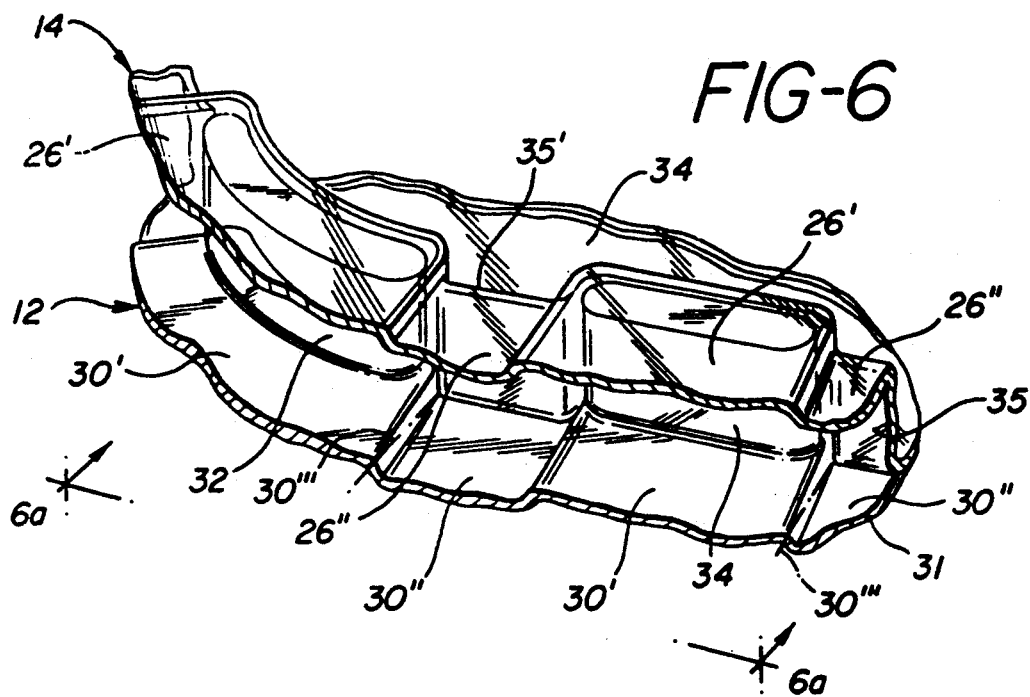
FIG. 6 is an enlarged view of the suture wrapping area of a suture package which eliminates the suture catching problem.

In accordance with the principles of the present invention, a solution to this suture catching problem is shown in FIG. 6. The solution is to alternately raise and lower the top and bottom of the suture wrapping channel 30, which causes the wrapped suture filament to bridge the areas where it may become caught in the mating channel edges. The curved lug 32 and the straight lug 34 are seen to smoothly blend into raised channel floor areas 30'. On either side of these raised areas the channel floor is lowered as shown by areas 30". Similarly, the projections 35 and 35' formed in the mating top piece 14 blend into lowered channel top areas 26". Where the upper surface 26 of the top piece overlies the lugs 32 and 34 to form the top of the channel, these portions of the channel top are raised as shown at 26'. These alternating raised and lowered areas cause the suture filament to bridge the mating edges where the filament can become entrapped between the two pieces of the package.

While the depressed floor areas 30" in FIG. 6 are shown as uniformly depressed across the width of the channel, it is preferable when using the aforementioned stylus winding technique to vary the depth of the depression across the width of the channel, as indicated by dashed line 30'''. The depressed floor area 30" will then be level with the surrounding floor areas 30' at the outer wall of the channel, and attain its maximum depression at the inner wall. This sloping of the depressed floor areas will provide a smooth floor at the outer periphery of the floor along which the stylus may smoothly travel during winding, while maintaining the depression at the inner wall which prevents the suture catching problem.

Figure 5A:
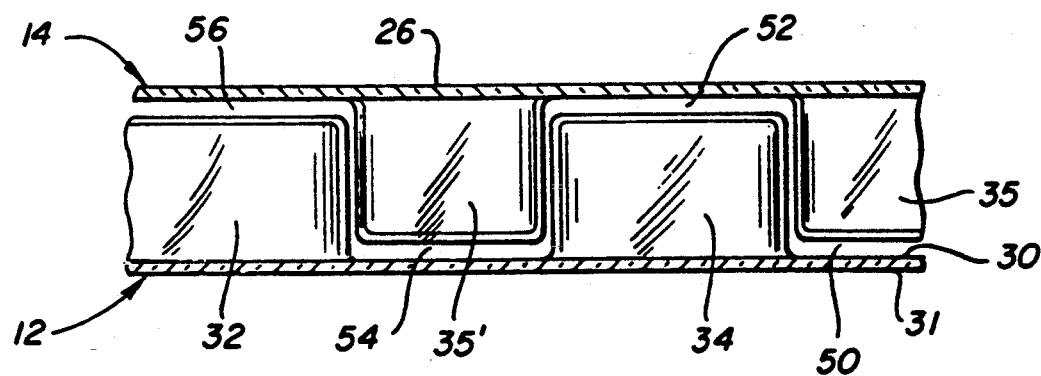
FIG. 5a is a cross-sectional view of the suture wrapping area of FIG. 5.
Figure 6A:
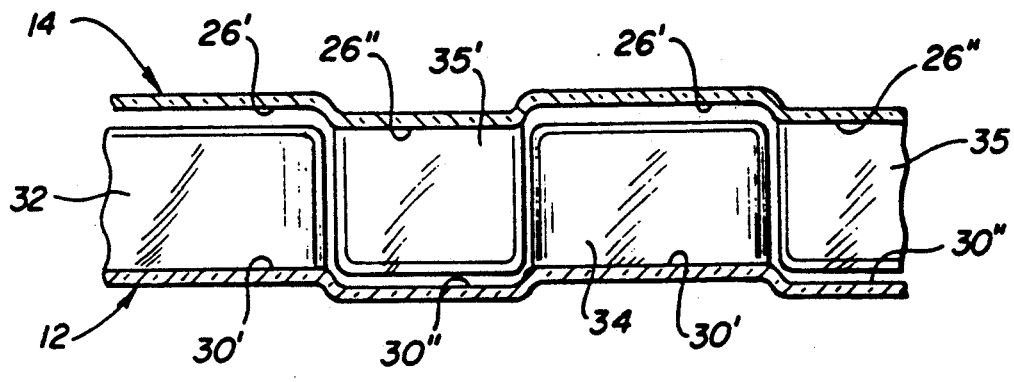
FIGS. 6a and 6b are cross-sectional views of the suture wrapping area of FIG. 6.
Figure 6B:
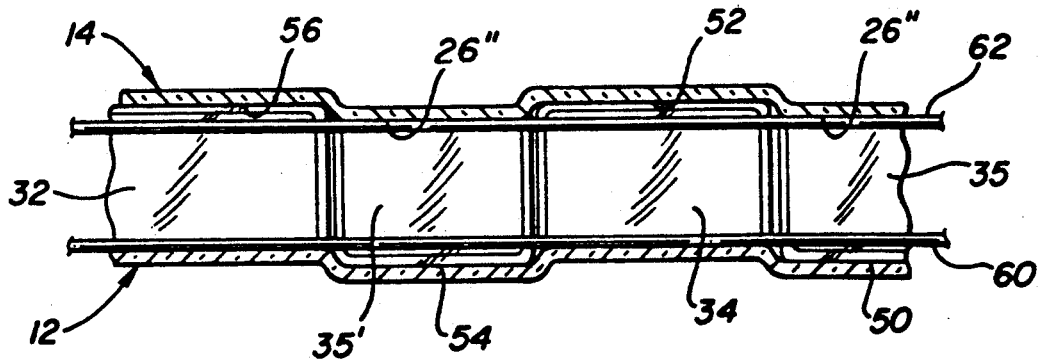

This result can be more fully appreciated by referring to the cross-sectional views of the channel 30 shown in FIGS. 5a, 6a, and 6b. FIG. 5a shows the top piece 14 of FIG. 5, including the upper surface 26 and projections 35 and 35', just as the top piece is about to mate with the bottom piece of the suture package. The interlocking bottom piece 12, including the lugs 32 and 34 and the channel floor 31, is shown below the top piece. The mating edge regions 50, 52, 54, and 56 where the suture filament may become pinched are clearly visible just before the two pieces interlock.

FIG. 6a shows the two package pieces of FIG. 6 with the raised and lowered channel floor and top sections just before mating. The projections 35 and 35' from the top piece 14 are seen to mate into the lowered floor sections 30", and the lugs 32 and 34 are seen to mate into the raised channel top sections 26'. Intermediate these sections the floor is alternately raised and the top is alternately lowered as shown at 30' and 26", respectively. As FIG. 6b illustrates, the alternately raised and lowered sections cause the suture filament 60 and 62 to bridge the areas 50–56 where the filament can become pinched between the mating pieces either during assembly of a pre-wound suture package or during suture withdrawal due to the capstan effect.

It has been found that another suture catching problem can occur when using the suture packages of FIGS. 1 or 3. As the suture is pulled through the channel 30 and unwinds, the free end of the suture will straighten out and extend to the outer wall of the channel formed by the overlapping surfaces 28 and 22. It has been discovered that the end of the suture can become caught under the bottom edge of the wall surface 28 or between the outer surface of wall 28 and the inner surface of wall 22. The problem is especially acute when a substantial length of the end of the suture filament becomes caught along the straight lengthy side of the channel 30.

Figure 9A:
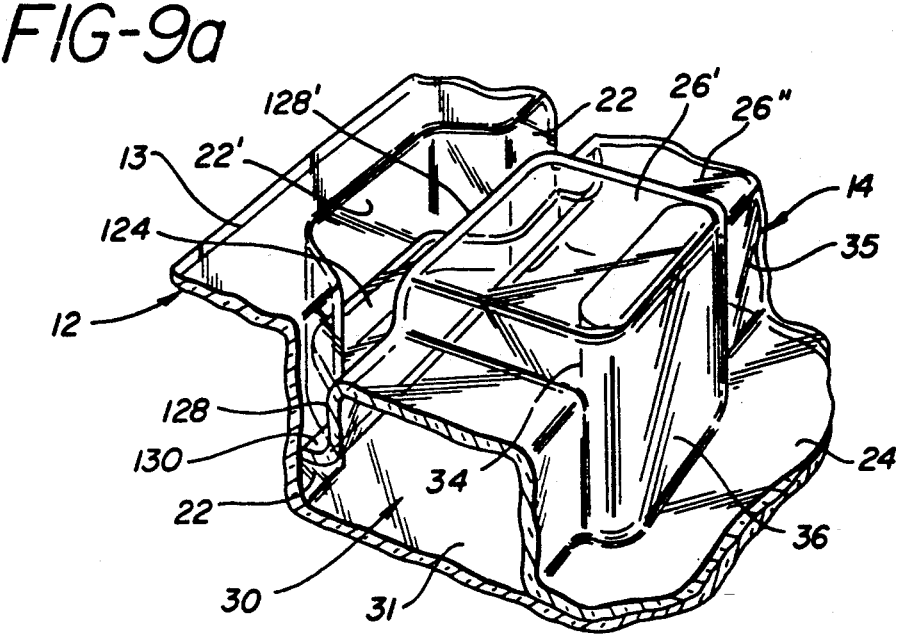
FIGS. 9 and 9a illustrate the periodically recessed outer wall of a suture wrapping channel in a suture package of the present invention.
Figure 9:
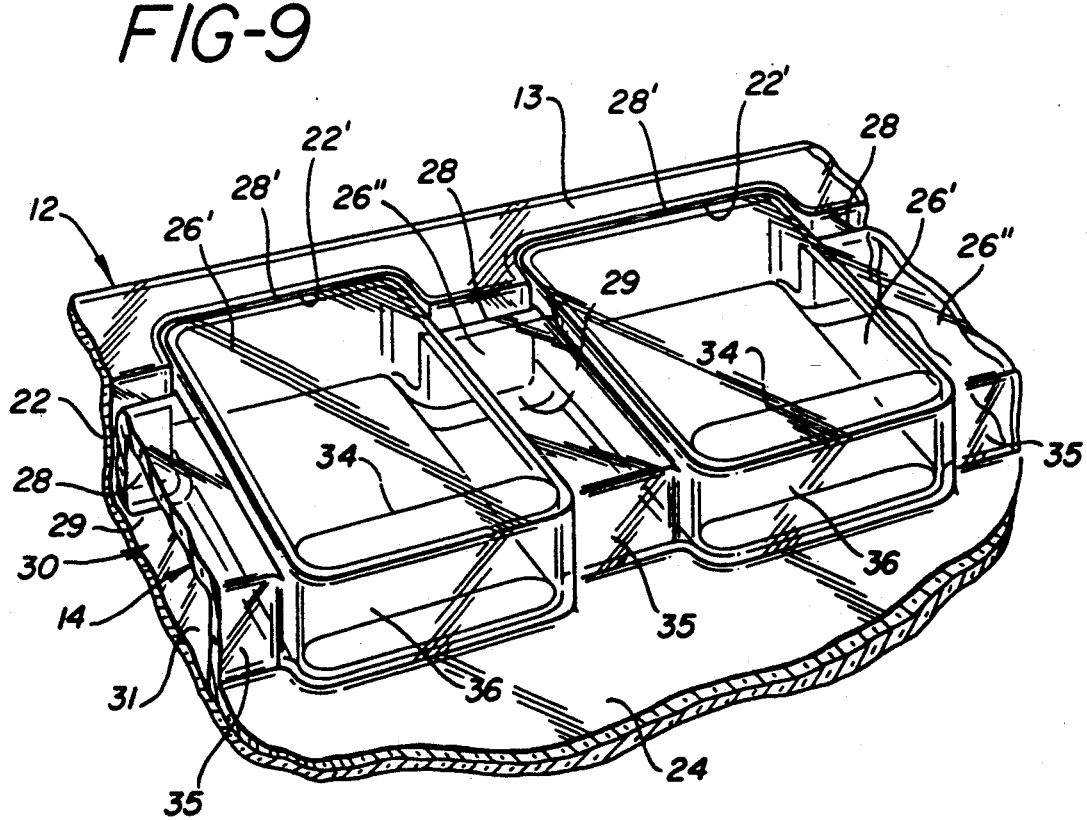

In accordance with a further aspect of the present invention, the problem of suture catching along the overlapping outside walls of the channel is minimized by alternately recessing the outer walls of the top and bottom pieces of the suture package as illustrated in FIG. 9. This FIGURE shows a section of the bottom piece 12 with its top outer flange 13 and floor 31 connected by the outer wall surface 22. Fitting within the wall surface 22 is the overlapping wall surface 28 of the top piece, which is joined at its upper edge to the upper surface 26 of the top piece. It may be seen that the two wall surfaces 22 and 28 are periodically recessed in tandem as indicated at 22' and 28'. As the suture end slides along the outer wall, it may enter the small spaces 29 below the lower edge of the wall 28. However, because these entrapping spaces 29 do not continue in a straight line, but are interrupted where the outer wall is recessed at 28' and 22', the end of the suture is unable to become entrapped under a substantial length of the lower edge of the outer wall 28. The relatively short lengths of the projecting wall sections 28 are inadequate to trap the end of the suture with any substantial retentive force, and hence the suture filament will pull smoothly from the suture package.

It has been found that, when a suture package with the alternately raised and lowered floor sections is wound with a suture from a suture-carrying stylus inserted between the outer walls 22 and 28, the stylus will bump up and down as it travels along the uneven floor of the channel. To prevent this occurrence in the embodiment of FIG. 9, the outer wall 28, 28' is modified by the addition of a lateral flange as shown in FIG. 9a. In this FIGURE it may be seen that the outer wall 128 is not flush with the surface of outer wall 22, but is offset from wall 22 by a lateral flange 130. Similarly, the outer wall 128' is offset from outer wall 22' by a bottom lateral flange 124. The lateral flanges 130 and 124 are in the same plane, and extend continuously around the outer periphery of the channel 30. When the suture-carrying stylus is inserted between the walls 22, 128 or 22', 128, it will track along the surface of the flanges 130, 124 as it travels around the periphery of the channel. The stylus will thus travel smoothly in the same plane about the channel.

Figure 7A:
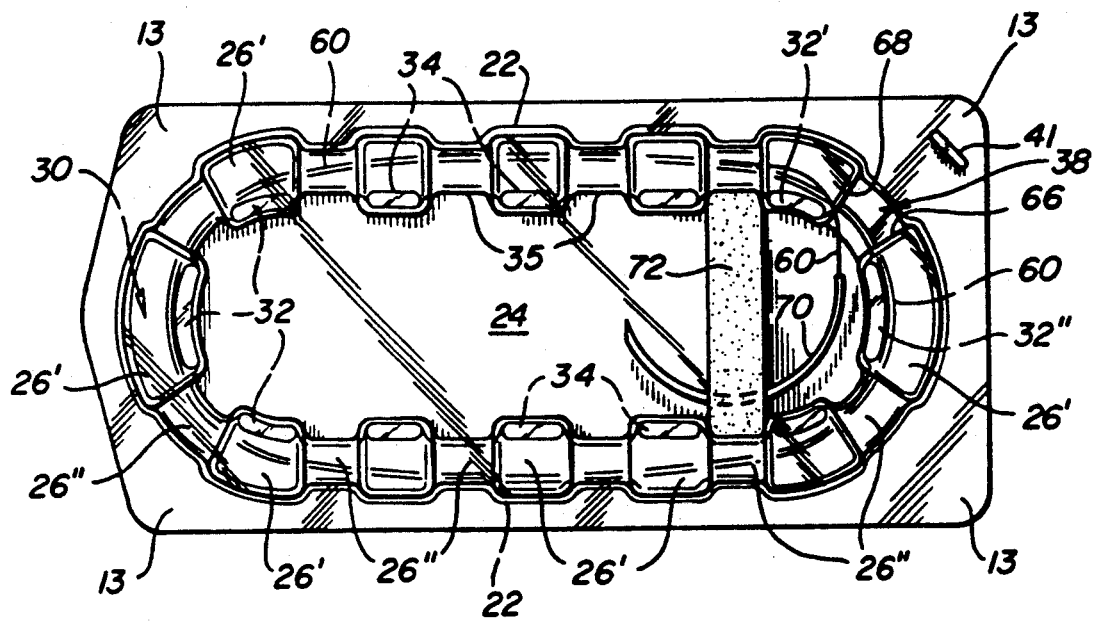
FIGS. 7a-7d illustrate various views of a preferred oval suture package of the present invention.

A preferred oval suture package constructed in accordance with the present invention is shown in FIGS. 7a-7d. FIG. 7a illustrates a top plan view of the package, in which the suture filament 60 is seen wound in the channel 30. The channel 30 is surrounded by the sealing flange 13 of the bottom piece 12 extending outward from the channel and in a plane near the upper planar surface of the package. The central floor area 24 of the top piece 14 is recessed to contact the similarly recessed central area 31 of the bottom piece 12. The inner wall of the channel 30 is defined by the curved lugs 32, 32', and 32" and the straight lugs 34 formed in the bottom piece 12. The projection 41 for the package peel tab is shown at the upper right corner of the package. The outer periphery of the top piece which forms the channel top is raised at 26' where the lugs are located, and is depressed over channel areas 26" between the lugs. The section of the top piece between lugs 32' and 32" is cut away at edges 68 and 66 to form an opening where the needle 70 attached to the suture 60 exits the channel 30. This exit area is shown more clearly in the enlarged view of FIG. 7c, where the edge 68 is seen to retain the needle 70 in the center (i e., from top to bottom) of the channel 30. The needle is held in place in the central area 24 of the package by the foam needle park 72. The needle may be held by the needle park 72 either by piercing the foam as indicated in FIG. 7a, or by insertion in a slit cut into the foam.

Figure 7B:
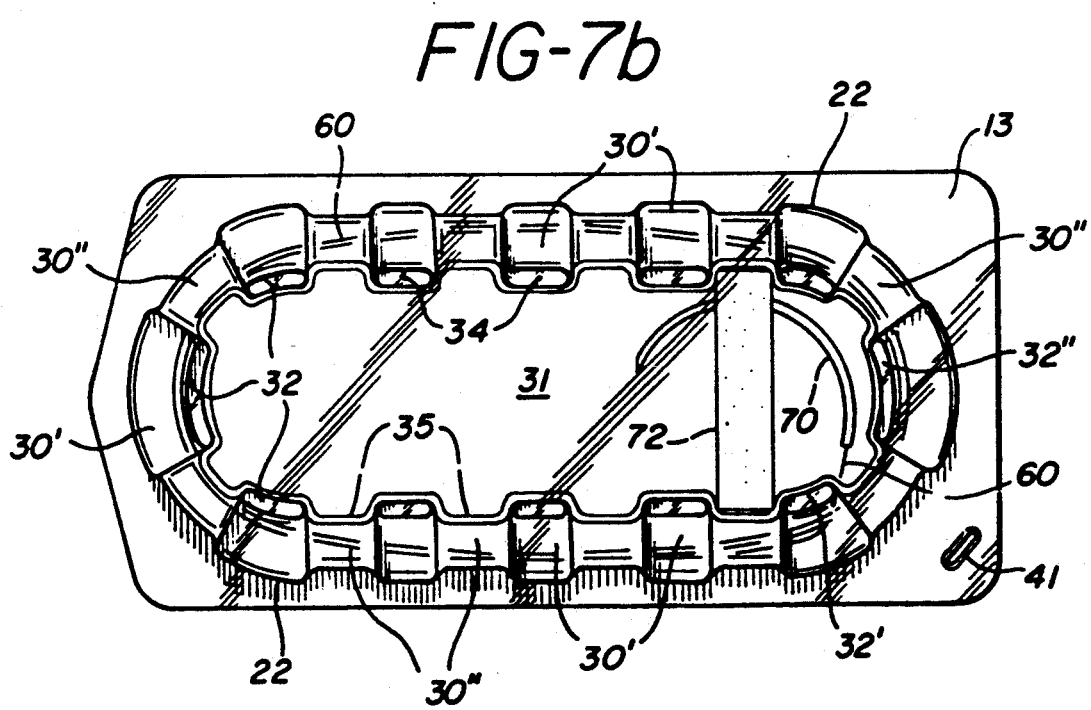

A plan view of the bottom of the suture package of FIG. 7a is shown in FIG. 7b. The central area 64 of the bottom of the package is in the same plane as the channel sections 30", which extend outward in alignment with the projections 35 of the top piece 14. The sections 30" of the bottom piece form the lowered floor sections of the channel 30, and the raised floor sections 30' are in alignment with the lugs of the bottom piece.

Figure 7C:
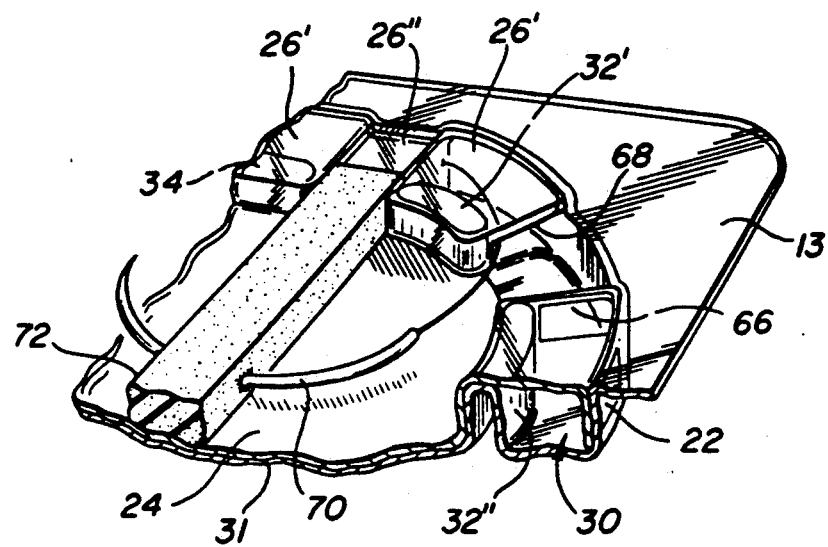
Figure 7D:
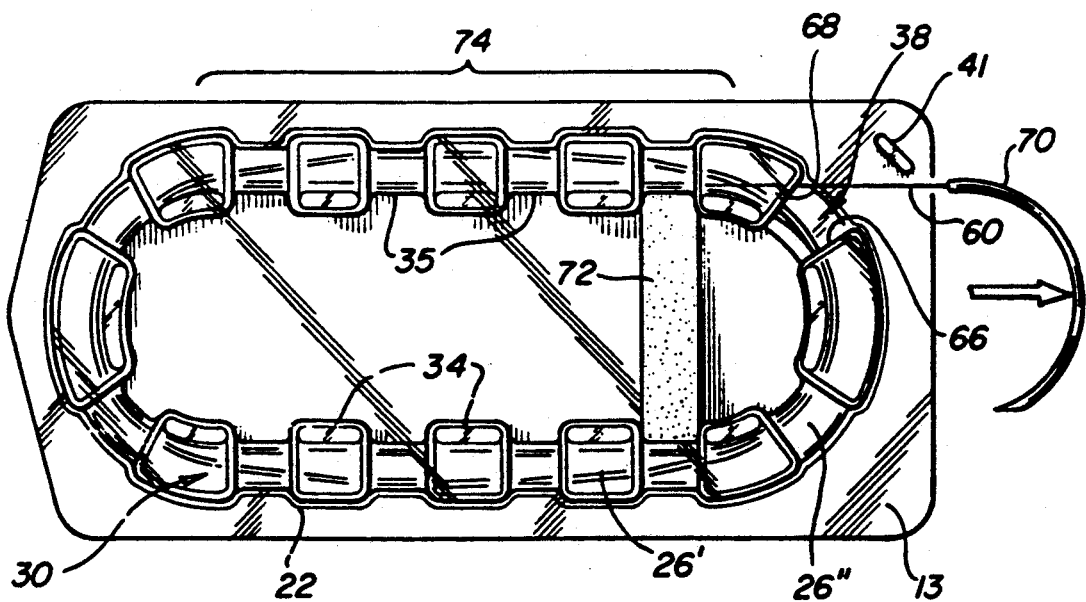

During use, the needle and suture are conventionally withdrawn from the suture package by grasping the body of the needle with a forceps. The needle is then pulled to withdraw the suture from the package as shown in FIG. 7d. As FIG. 7d shows, the cutaway 38 for the suture exit from the channel 30 is preferably located at the juncture of an oval end of the package with a straight section 74 of the oval channel. It may be seen that the suture is wound so that the suture will exit the channel 30 in a straight line with the long straight side 74 of the oval. By pulling the suture from a straight section of the oval rather than from a curved oval end of the channel, binding and frictional resistance of the suture at it unwinds from the channel 30 is minimized.

In the embodiment of FIG. 7d this is accomplished by locating the edge 68 of the cutaway opening 38 so that the suture is withdrawn in a straight line from the inside wall (32, 35) of the straight channel section 74 and through the opening 38.

Figure 8A:
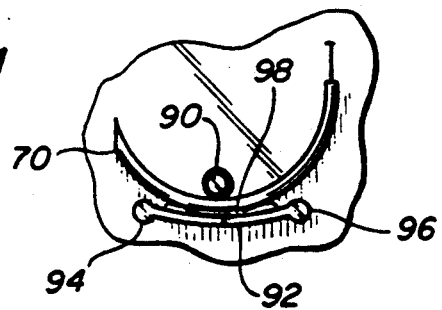
FIGS. 8a and 8b illustrate a molded needle holder.
Figure 8B:
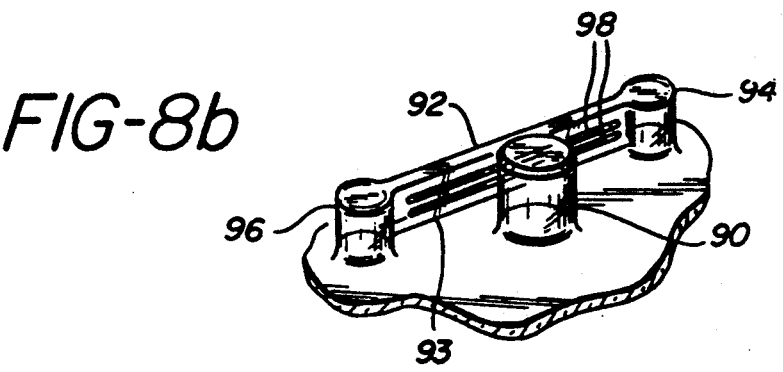

An alternate means for retaining the needle within the suture package, or needle "park", is illustrated in FIGS. 8a and 8b. This needle park comprises a molded projection or post 90 located in the depressed central area 24 of the top piece 14 of the package. Adjacent the post 90 is a molded rail 92 with end supports 94 and 96. Taking advantage of the precise tolerances which may be maintained by the molding process, the rail 92 is spaced apart from the post 90 by a distance which is slightly smaller than the diameter of the needle 70. The needle 70 is retained in place by contact on either side of the needle with the post and the rail. Because the rail is relatively thin and formed of the polymeric material of the package, it is resiliently flexible and will bend to accommodate placement of the needle between the post and rail. FIG. 8a is a plan view of the needle 70 when placed between the post and rail, which causes the rail to flex slightly and hold the needle in place. FIG. 8b is an enlarged view of the post 90, rail 92 and supports 94 and 96.

While the needle park of FIGS. 8a and 8b is shown to be formed on a single molded surface such as the floor 24 of the suture package, portions of the needle park may be formed on both package pieces. The post 90 could be molded in the floor 31 of the bottom piece 12, and would extend through a hole cut in the floor 24 of the top piece 14. To enhance the flexibility of the rail 92, the bottom edge of the rail need not be connected to the underlying floor, but may be separated as by an opening formed beneath the rail as indicated at 93. To assure retention of the needle in the needle park, the opposing surfaces of the rail 92 and the post 90 may include a plurality of thinly formed ribs 98 as shown in FIG. 8b.

Figure 10:
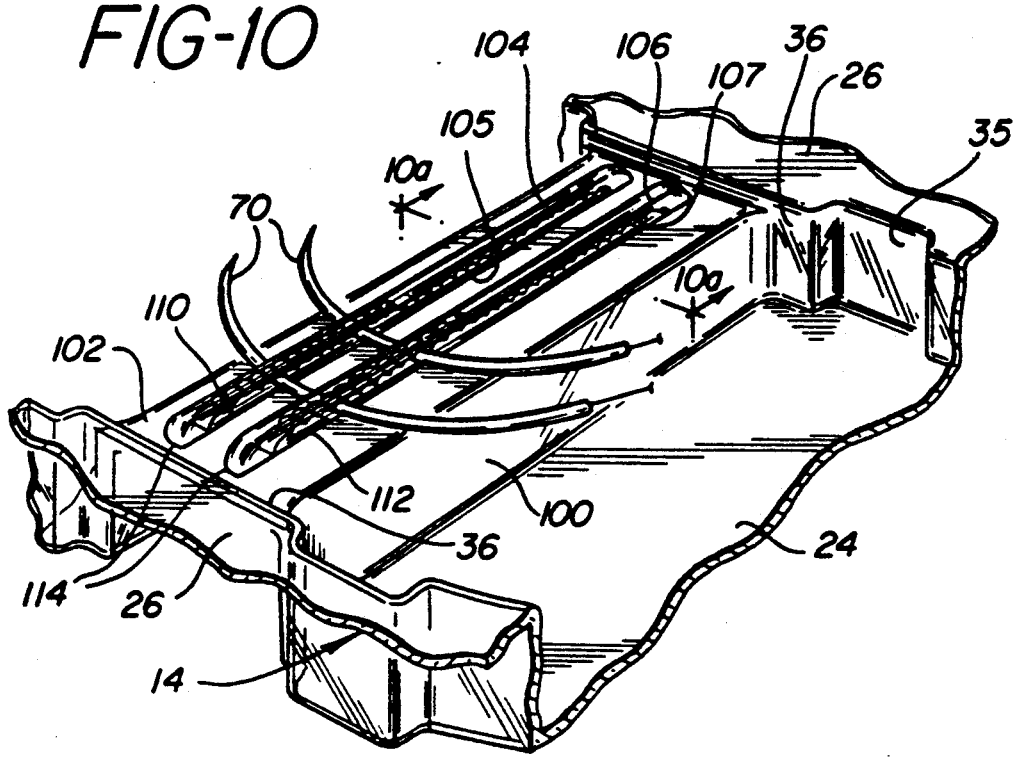
FIGS. 10 and 10a illustrate in perspective and cross-sectional views a second molded needle holder.
Figure 10A:
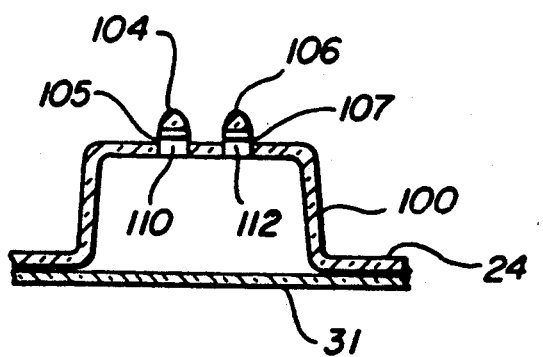

Another molded needle park is shown in FIGS. 10 and 10a. The needle park of FIG. 10 is molded as a part extending upward from the depressed central area 24 of the top piece 14. The needle park comprises a Platform 100 extending across the central area 24 of the top piece 14, between the inner walls of the channel in the location of the foam pad 72 of FIG. 7a, discussed below. Attached to the top surface of the platform 100 are two string-like lengths 104 and 106 of the molded material. These strings are affixed at their ends to the top surface 102 of the platform. Formed in the bottom surfaces of the strings are tooth-like notches indicated at 105 and 107. The top 102 of the platform is open below the strings 104 and 106 as indicated at 110 and 112 to simplify the molding of the top piece.

Needles are parked in the needle park of FIG. 10 by insertion under the strings 104 and 106 and on top of the platform 100. The notches 105 and 107 prevent the inserted needles 70 from sliding in the direction of the length of the strings after insertion. The top 102 of the platform is recessed to a level below the upper surface 26 of the package top so that the top of the strings do not project above the level of the upper surface 26 after the needles have been inserted. Thus, the strings will not project upward to, or interfere with, the sealing of the overwrap across the top surface 26 of the suture package. Since the strings 104 and 106 are formed of the polymeric molding material, they are flexible so as to expand upward and back downward to hold the inserted needles securely in place. This needle park arrangement is capable of retaining needles of gages ranging from 8 mils to 42 mils.

Instead of inserting the points of the needles under the strings when they are parked, it may be easier to park them by sliding the central length of the needles under the strings from the ends of the strings. To enable this technique of needle insertion, an end of each needle is disconnected from the top surface 102 of the platform as indicated at 114. A needle is then parked by placing it on top of the platform surface 102 at the detached ends of the strings, then sliding the needle across the surface 102 and under the strings.

A cross-sectional view of the needle park of FIG. 10 is shown in FIG. 10a. This view clearly shows the platform 100 extending upward from the depressed central area 24 of the top piece. The strings 104, 106 and their underlying open areas 110, 112 are also clearly shown in cross-section.

Instead of forming the needle park of FIGS. 10 and 10a solely on the floor 24 of the top piece, the platform 100 can be molded on the floor 31 of the bottom piece and the strings 104, 106 can be molded in the top piece. The platform 100 extends through an opening formed in the overlying floor 24, and the strings are formed above this opening, stretching between the walls 36 of the channel. The needles may then be placed on the top surface 102 of the platform 100, and will be held in place when the top piece is mated with the bottom piece, which brings the extended strings down into contact with the needles.

The suture package pieces 12 and 14 of the present invention may be formed by molding processes such as injection molding or thermoforming. The pieces may be made of any surgically compatible polymeric materials, such as polyester plastic, PET-G polyethylene, polyvinyl chloride (PVC), polypropylene, or polystyrene. The preferred technique for assembling the package is to first affix the top and bottom pieces together and attach the needle park if the foam-style needle park is employed.

The preferred technique for winding the suture filament 60 through the channel is to insert the end of the suture into a stylus S which will travel through the channel between the overlapping outer walls of the top and bottom pieces 12,14, as better seen in FIG. 1. Prior to winding the suture 60 the needle 70 is inserted in the needle park 72, as seen in FIG. 7c. The suture filament is then wound around the channel starting from the end of the suture 60 which is attached to the needle 70. When the suture is fully wound within the channel, there is derived the wound form of suture 60 as seen, for instance in FIG. 7b.

The present inventors have experimented with several winding techniques, including winding the end portion of the suture around the interior "capstan" of the channel first, and winding the suture portion which is closest to the point of attachment to the needle around the capstan first. It was found that, when the loop at the end of the suture was most interior in the channel (i.e., against the center capstan of the oval), and the loop at the point of needle attachment was the outermost loop of the wound suture, the suture would bind during withdrawal. This would occur as the outer loop being withdrawn first would tighten against the loops inside it, effectively pinning the underlying loops against the capstan in the center of the oval.

To prevent this binding problem, the suture filament is wound through the channel so that the loop closest to the point of needle attachment (the loop which is withdrawn first from the suture package) is the most interior loop, located closest to the center of the channel. Loops of suture located progressively toward the free end of the suture are disposed sequentially toward the outer periphery of the channel, with the free end of the suture at the outside of the channel. Thus, when the suture is withdrawn from the package, the first loop withdrawn will dispense from the capstan. The next loop will then tighten toward the capstan and similarly be dispensed therefrom. With the loops progressively moving inward to the capstan as they are withdrawn, there will be no binding caused by the pinning of a loop of suture filament against the capstan by the loop being withdrawn. Loops to be subsequently withdrawn will move freely around the periphery of the channel as the loop being withdrawn is dispensed from the interior capstan.

It may be appreciated that the oval wrapped suture package of the present invention imparts very little "set", or "memory" to the wound suture as compared, for instance, to a conventional figure-8 or other winding pattern with numerous loops and tight bends. The only curves to the winding pattern are the semicircular turns at the ends of the oval shape, which are made over almost the full width of the rectangular package. The sides of the oval channels may, in a modified embodiment, also be gradually curved outward as the suture filament passes from one end of the oval to the other in the shape of a "0". However, such a pattern may unacceptably widen the rectangular package or require a tighter curvature of the winding than the semicircular 180° end turns of the package of the preferred embodiment. It has been found that the oval shape with straight sides connecting the semicircular ends will result in a filament memory with straight filament segments between arcuate sections, an acceptable shape for a surgical filament. The preferred oval shape in a rectangular package is an optimal compromise of the objectives of minimal suture memory, smooth tangle-free withdrawal, and minimal package width for efficient packaging of a number of suture packages.

What is claimed is;

1. A method for winding a suture filament in an oval channel of a suture package, said suture filament being attached to a needle at one end and having a second, free end, comprising the steps of winding said filament through said channel ending with its free end and, after the filament is substantially entirely wound in said oval channel, attaching the needle to a needle park location on the package, wherein the step of winding comprises attaching said filament to a stylus at a point in the proximity of its free end, then causing said stylus to travel through said channel to wind said filament through said channel.

2. The method of claim 1, wherein the step of attaching the needle comprises attaching the needle to a needle park location in the center of said oval channel.

3. A method for winding a suture filament in an oval channel of a suture package, said suture filament being attached to a needle at one end and having a second, free end, comprising the steps of attaching the needle to a needle park location ion the package and then winding said filament through said channel ending with its free end until said filament is substantially entirely wound in said oval channel, wherein the step of winding comprises attaching said filament to a stylus at a point in the proximity of its free end, then causing said stylus to travel through said channel to wind said filament through said channel.

4. The method of claim 3, wherein the step of attaching the needle comprises attaching the needle to a needle park location in the center of said oval channel.

* * * * *